(12) United States Patent
Slavin et al.

(10) Patent No.: US 7,472,588 B2
(45) Date of Patent: Jan. 6, 2009

(54) PETROPHYSICAL FLUID FLOW PROPERTY DETERMINATION

(75) Inventors: Vyacheslav I Slavin, Berlin (DE); Yury Budansky, Oakland, NJ (US); Leonid Levitan, Brooklyn, NY (US); Walter Breidenstein, Boyne Falls, MI (US)

(73) Assignee: Sorowell Production Services LLC, Walloon Lake, MI (US)

( * ) Notice: Subject to any disclaimer, the term of this patent is extended or adjusted under 35 U.S.C. 154(b) by 83 days.

(21) Appl. No.: 11/736,748

(22) Filed: Apr. 18, 2007

(65) Prior Publication Data

US 2008/0257030 A1    Oct. 23, 2008

(51) Int. Cl.
*E21B 49/00* (2006.01)
*G01V 3/00* (2006.01)

(52) U.S. Cl. .................................. 73/152.11; 324/376

(58) Field of Classification Search .................. 73/863, 73/865.6, 152.11; 324/376
See application file for complete search history.

(56) References Cited

U.S. PATENT DOCUMENTS

| | | | | |
|---|---|---|---|---|
| 2,296,852 A | * | 9/1942 | Horner | 73/38 |
| 2,641,922 A | * | 6/1953 | Smith | 73/19.05 |
| 3,302,101 A | * | 1/1967 | Glanville | 324/376 |
| 4,380,930 A | * | 4/1983 | Podhrasky et al. | 73/594 |
| 4,546,318 A | * | 10/1985 | Bowden | 324/376 |
| 4,628,267 A | * | 12/1986 | Lee et al. | 324/376 |
| 4,663,711 A | * | 5/1987 | Vinegar et al. | 702/12 |
| 4,907,448 A | * | 3/1990 | Givens | 324/376 |
| 4,926,128 A | * | 5/1990 | Givens | 324/376 |
| 4,996,421 A | * | 2/1991 | Rai et al. | 250/255 |
| 5,012,674 A | * | 5/1991 | Millheim et al. | 73/152.03 |
| 5,027,379 A | * | 6/1991 | Hunt et al. | 378/4 |
| 5,105,154 A | * | 4/1992 | Givens et al. | 324/376 |
| 5,164,590 A | * | 11/1992 | Coles et al. | 250/255 |
| 5,164,672 A | * | 11/1992 | Gilliland et al. | 324/376 |
| 5,209,104 A | * | 5/1993 | Collins et al. | 73/38 |
| 5,417,104 A | * | 5/1995 | Wong | 73/38 |
| 5,493,226 A | * | 2/1996 | Honarpour et al. | 324/376 |
| 5,503,001 A | * | 4/1996 | Wong | 73/38 |
| 5,670,041 A | | 9/1997 | Cho et al. | |
| 5,679,885 A | * | 10/1997 | Lenormand et al. | 73/38 |
| 5,844,136 A | * | 12/1998 | Marsala et al. | 73/38 |
| 6,247,358 B1 | * | 6/2001 | dos Santos | 73/152.11 |
| 7,051,817 B2 | | 5/2006 | Shaposhnikov et al. | |
| 7,143,653 B2 | * | 12/2006 | Abdel-Hadi et al. | 73/819 |
| 7,147,058 B1 | | 12/2006 | Shaposhnikov et al. | |
| 7,319,332 B2 | * | 1/2008 | Lenormand et al. | 324/376 |
| 2006/0213652 A1 | | 9/2006 | Shaposhnikov et al. | |

OTHER PUBLICATIONS

Chernikov K.A., Slavin V.I., Aristarov M.G.; Dictionary On Geology Of Oil And Gas (Bowels, 1988, p. 226).

(Continued)

*Primary Examiner*—Hezron Williams
*Assistant Examiner*—John Fitzgerald
(74) *Attorney, Agent, or Firm*—Brooks Kushman P.C.

(57) ABSTRACT

A method and apparatus for determining petrophysical parameters within a geologic formation pressurizes a geologic sample through a set of predetermined effective pressures, energizes the sample at each predetermined effective pressure with an electric current and/or sonic energy, and measures a conductivity value (electrical conductivity and/or sonic velocity). Permeability and/or porosity are also measured at each pressure through a traditional method and the functions are compared so that permeability and/or porosity can be subsequently derived from a sonic or electrical measurement of a comparable sample under a effective pressure. An apparatus is also described for acquiring the measurements under tri-axial compression, with a computerized interface in one embodiment.

20 Claims, 6 Drawing Sheets

OTHER PUBLICATIONS

M.D. Belonin, V.I. Slavin, D.V. Chilingar; Abnormal Pressures. Origins, Prediction, Problems Of Development Of Hydrocarbon Fields; St. Petersburg, Nedra, 2005, pp. 66-68, 73-75, 169, 170.

Sitnikov M.F., Volik A.L., and Kuksov A.K.; The Results Of The Research Of Rock Samples Deformation At Secondary Consolidation (Journal of "Drilling", 1971. No. 9, pp. 33-36).

* cited by examiner

PETROPHYSICAL FLUID FLOW PROPERTY DETERMINATION

FIELD OF THE INVENTION

The invention relates to determination of petrophysical parameters of geologic samples (simple carbonate and clastic rocks and complex fractured carbonate and clastic rocks) respective to exploitation of oil and gas deposits during the search and exploitation of petroleum deposits. Focal use of the invention is directed to providing accurate petrophysical parameters database values (permeability, porosity and the like) for rock samples from a geologic structure, and also for rapidly evaluating petrophysical parameters of a geologic structure during seismic work and/or geophysical research respective to wellbores.

BACKGROUND

Oil and gas recovery from wells is a key technology in providing for modern energy needs. As an oil pool is depleted, the characteristics of the fluids and rock formation being accessed by the well modify with commensurate impact on the efficiency of oil harvesting. Various systems have been created to manage issues in this concern. Some systems for use in this regard are described U.S. Pat. No. 7,051,817; U.S. Pat. No. 7,147,058; and also US Patent Application 2006/0213652. All of these patents and patent applications are hereby incorporated by reference herein. The patents bring forth various interrelated issues in management of pressure, oil field reservoir characterization, entrained gas, entrained water, augmented pumping, and the like respective to the interface between the bottom hole of an oil well and the pumping system used to remove the oil.

In determining oil field reservoir status, various methods for determining petrophysical parameters (e.g., porosity) of rocks have been previously described. One traditional method tests a geologic sample of rock under atmospheric pressure to derive a porosity value. One drawback to this traditional method is that the porosity in the actual pressurized rock (under geologic pressure forces) is different than the porosity at atmospheric pressure. A further method is described by Chernikov K. A., Slavin V. I., Aristarov M. G., etc. in the Dictionary On Geology Of Oil And Gas (Bowels, 1988, 679 p.). In this second method for defining porosity, an acoustic impulse seismic evaluation of a wellbore uses the time interval between an acoustic impulse and its reflected acoustic wave to derive a porosity value for comparison with a traditionally-determined porosity value from the measured geophysical parameters for different types of rocks.

In yet another method (M. D. Belonin, V. I. Slavin, D. V. Chilingar; Abnormal Pressures. Origins, Prediction, Problems Of Development Of Hydrocarbon Fields; St. Petersburg, Nedra, 2005, 324 pp.), the depth of a deposit is factored into the porosity determination. This article brings forward the issue of effective pressure (respective to the depth of a rock formation) and its impact on the petrophysical parameter measurements respective to either irreversible deformation behaviour (at a depth effectively below a critical elastic deformation depth value) in the rock or elastic deformation (at a depth effectively shallower than the critical elastic deformation depth value).

A triaxial compression method is discussed by Sitnikov M. F., Volik A. L., and Kuksov A. K., in The Results Of The Research Of Rock Samples Deformation At Secondary Consolidation (Journal of "Drilling", 1971. Number 9, pages 33-36). Triaxial pressure gradually compresses a sample, and a functional relationship between sample length and compression time is derived. The measured parameters are converted into, for example, permeability according to the Darcy equation. Empirical results have show an inflection point in an otherwise linear functional relationship where the rock presumably undergoes a clear structural aspect shift in density—presumably a compromise in rigidity of the supporting walls of microcavities (pores) in the rock.

One drawback of independently-administered methods is that interdependences respective to permeability, porosity, and fluid flow are not defined during the method implementation and thereby do not provide a comprehensive predictor of fluid flow characteristics. Existing methods also tend to achieve the best results for simple carbonate and clastic rocks, which are insignificantly fractured. What is needed is a method and system for fully defining petrophysical parameters (permeability, porosity and the like) of a broad spectrum of rocks (simple carbonate and clastic rocks and complex fractured carbonate and clastic rocks) under influence of effective pressure at both irreversible and elastic deformation depths. Another need is for rapid determination of permeability status of geological structure samples in an operating oil well.

SUMMARY

The invention provides a method for determining petrophysical parameters within a geologic formation. The method comprises: obtaining a geologic sample from the geologic formation; pressurizing (uni-axially or tri-axially) the geologic sample to a predetermined effective pressure; energizing the geologic sample at the predetermined effective pressure with an energy wave such as an electric current and/or sonic energy in the form of a sonic wave; measuring a conductivity value (electrical conductivity and/or sonic velocity) in the geologic sample respective to the energizing at the predetermined effective pressure; and repeating the pressurizing, energizing, and measuring steps over a number of predetermined effective pressures to provide a set of conductivity measurements as a function of the effective pressures for the geologic sample.

In another embodiment, permeability measurements of the geologic formation are measured at the effective pressures to provide a set of porosity measurements as a function of effective pressures for the geologic sample. In yet a further embodiment, porosity measurements of the geologic formation are determined at the effective pressures to provide a set of permeability measurements as a function of effective pressures for the geologic sample.

In one aspect, the functional relationship has an affiliated inflection point defining a maximum effective pressure for the geologic formation. In another aspect, where the geologic formation has an elastic deformation depth value, the obtaining further measures the depth of the geologic sample in the geologic formation, and, in the repeating, the predetermined effective pressures incrementally increase when the geologic sample depth is less than the elastic deformation depth value. In yet another aspect, the predetermined effective pressures incrementally decrease when the geologic sample depth is greater than the elastic deformation depth value.

In yet a further embodiment, the method further comprises positioning a sonic transmitter and sonic receiver at a depth in the geologic formation; measuring a test conductivity value at the evaluating effective pressure; and defining a permeability value for the geologic formation using the test conductivity value, the set of permeability measurements, and the set of conductivity measurements.

In yet a further embodiment, the method further comprises obtaining a second geologic sample from a depth in the geologic formation; pressurizing the second sample to an evaluating effective pressure representative of pressure at the depth; measuring a test conductivity value at the evaluating effective pressure; and defining a permeability value for the second geologic sample using the test conductivity value, the set of permeability measurements, and the set of conductivity measurements.

In a further embodiment, an apparatus is provided for measuring fluid flow capability within a geologic sample. The apparatus comprises: a housing having a housing inner surface defining a housing cavity; an elastic sample container within the cavity where the elastic sample container has an sample container internal surface and a movable piston in sealingly slideable interface to the internal surface, the piston has a sample contact surface, and the sample container and the sample container internal surface and the sample contact surface provide thereby a sample cavity; a hydraulic fluid in hydraulic linkage to the piston and disposed within the housing cavity to encapsulate the elastic sample container; at least one energy transmitter (such as an electrical contact and/or a sonic transmitter) disposed on a first portion of the sample container internal surface; at least one energy receiver (such as an electrical contact and/or a sonic receiver) disposed on a second portion of the sample container internal surface; a fluid conduit in fluid communication with the sample cavity for expelling fluid from the sample cavity; means for energizing each transmitter (electrical voltage source and/or sonic wave generator); means for measuring an energy signal from each energy receiver (electrical meter and/or sonic velocity determiner); and means for pressurizing the hydraulic fluid; where the sample is configured to snuggly fit within the sample cavity after the piston has been pressurized so that essentially all external surface portions of the sample are independently in contact with either the internal surface, the sample contact surface, the energy transmitter, or the energy receiver.

In other embodiments, the apparatus includes a traditional means for determining either porosity and/or permeability measurements for the geologic sample.

The novel features that are considered as characteristic for the present invention are set forth in particular in the appended claims. The invention itself, both as to its construction and its method of operation together with additional objects and advantages thereof, will be best understood from the following description of specific embodiments when read in connection with the accompanying drawings.

DETAILED DESCRIPTION OF THE PREFERRED EMBODIMENTS

The following definitions and non-limiting guidelines must be considered in reviewing the description of this invention set forth herein.

The headings (such as "Introduction" and "Summary") and sub-headings (such as "Amplification") used herein are intended only for general organization of topics within the disclosure of the invention, and are not intended to limit the disclosure of the invention or any aspect thereof. In particular, subject matter disclosed in the "Introduction" may include aspects of technology within the scope of the invention, and may not constitute a recitation of prior art. Subject matter disclosed in the "Summary" is not an exhaustive or complete disclosure of the entire scope of the invention or any embodiments thereof.

The citation of references herein does not constitute an admission that those references are prior art or have any relevance to the patentability of the invention disclosed herein. All references cited in the Description section of this specification are hereby incorporated by reference in their entirety.

The description and specific examples, while indicating embodiments of the invention, are intended for purposes of illustration only and are not intended to limit the scope of the invention. Moreover, recitation of multiple embodiments having stated features is not intended to exclude other embodiments having additional features, or other embodiments incorporating different combinations the stated of features.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the word 'include," and its variants, is intended to be non-limiting, such that recitation of items in a list is not to the exclusion of other like items that may also be useful in compositions, materials, devices, and methods of this invention.

The examples and other embodiments described herein are exemplary and not intended to be limiting in describing the full scope of compositions and methods of this invention. Equivalent changes, modifications and variations of specific embodiments, materials, compositions and methods may be made within the scope of the present invention, with substantially similar results.

The embodiments relate to comprehensive measurement of petrophysical parameters in geologic formations. The focal use of the derived parameters is generally related to oil recovery.

In overview as a general method, the embodiments progressively change the pressure (either triaxially or uniaxially) on a geologic sample obtained from a geologic formation while energizing the sample, at particular equilibrium points in the pressurizing (or depressurizing) of the sample, with one or more energy forms (such as, without limitation, an electrical current and/or sonic wave energy). The effect of each energy wave or energy form is measured, so that a co-coordinated set of measurements of these phenomena and traditional porosity and permeability measurements (see discussion of references in the Background) are defined for the range of effective pressures (effective pressure being the difference between imposed effective pressure and fluid pressure within the sample). In this regard, structural shifts in density of rock from pressurization affect, for instance, the effective sonic velocity and also the electrical conductivity of the formation even as the more mechanically measurable aspects of porosity and permeability are altered. Indeed, certain aspects of the particular local oil pool can also affect fluid flow through a rock formation; some of these aspects commensurately modify with pressure and are more readily determined by non-mechanical measurements such as electrical conductivity and/or sonic velocity measurements. When an electrical type of energy wave or an electric current energy wave is used herein for testing the geologic sample to determine a conductivity value for the geologic sample, the term energy wave includes an electrical impulse or current driven through either an alternating current circuit or a direct current circuit (AC electricity or DC electricity are considered herein to both manifest electrical waves, with a DC circuit frequently manifesting an electrical wave of extended wavelength). AC current frequency and sonic frequency are selected to provide readily measurable conductivity petrophysical parameter readings for a particular geologic sample and are then maintained as essentially constant for further comparative use of this measured data.

The formation needs to be measured and considered holistically as a multiphase and multicomponent combination of oil and other materials resistant within a porous and permeable rock structure. Insofar as flow of fluids within any permeable medium is impacted by variables such as viscosity, surface tension, and impurities as well as by physical measurements of the permeable medium, affiliated sonic and/or electrical data (or the like) is of potential value in characterizing anticipated petroleum flow behavior through the porous rock.

Additionally, in operation, a rapid manner for determining porosity and/or permeability in a geologic sample from the geological formation is usefully provided—a measurement of permeability via measurement of, for example, sonic velocity with reference to prior data showing the interrelationship of sonic velocity and permeability can be acquired more rapidly than a direct measurement of permeability from a sample. Therefore, once a representative set of petrophysical parameters is available for a particular geologic formation, a geologic sample can be acquired from a depth in that geologic formation, pressurized to an evaluating effective pressure representative of pressure at the depth, and measured at that test pressure for a test conductivity value (e.g., without limitation, electrical conductivity and/or sonic velocity). The representative set of petrophysical parameters then can be used to define a porosity/permeability value for that sample from the test conductivity value. In another embodiment, an energy transmitter and an energy receiver (such as a sonic transmitter and sonic receiver or two electrical contacts) can be positioned at a depth in the geologic formation and so that they bear against the geologic formation, a test conductivity value measured from the transmitter and receiver, and a permeability can be determined for the geologic formation using the test conductivity value, the prior set of permeability measurements for the geologic formation, and the set of conductivity measurements for the formation. In using the porosity/permeability value for the geologic formation permeability, it is also to be appreciated that fluid flow prediction from the use of the loci of FIGS. 1A and 1B is derived from a controlled sampling system according to any of FIGS. 2-5, and that such data may need some further interpretation to compensate for other factors near the wellbore due to effects such as physical vibration of the rock formation and/or electromagnetic field status.

The suggested method is therefore implemented by means of the additional measurements (additional to traditional mechanically-implemented permeability and porosity determinations) of the speed of distribution of elastic waves (or other non-destructive test impulses) at different predetermined effective pressures in a triaxial compression system (or in a uniaxial compression system). The acquired data is then plotted to provide a reference defining the dependence of speed of distribution of elastic waves (or other geophysical parameter) as a function of the effective pressure and, at least indirectly, as a function also of the traditionally-measured petrophysical parameters of permeability and/or porosity. If the effective pressure is unknown in subsequent measurements, the abovementioned functional dependencies for the particular geologic formation can then provide a basis for rapidly defining the petrophysical parameters (permeability, porosity and so on) of the particular geologic formation. The invention relates to the exploitation of oil and gas deposits; it is aimed at the evaluation of values of petrophysical parameters (permeability, porosity and so on) of the rocks in a geologic formation during the search and exploitation of petroleum deposits.

Figure 1A:
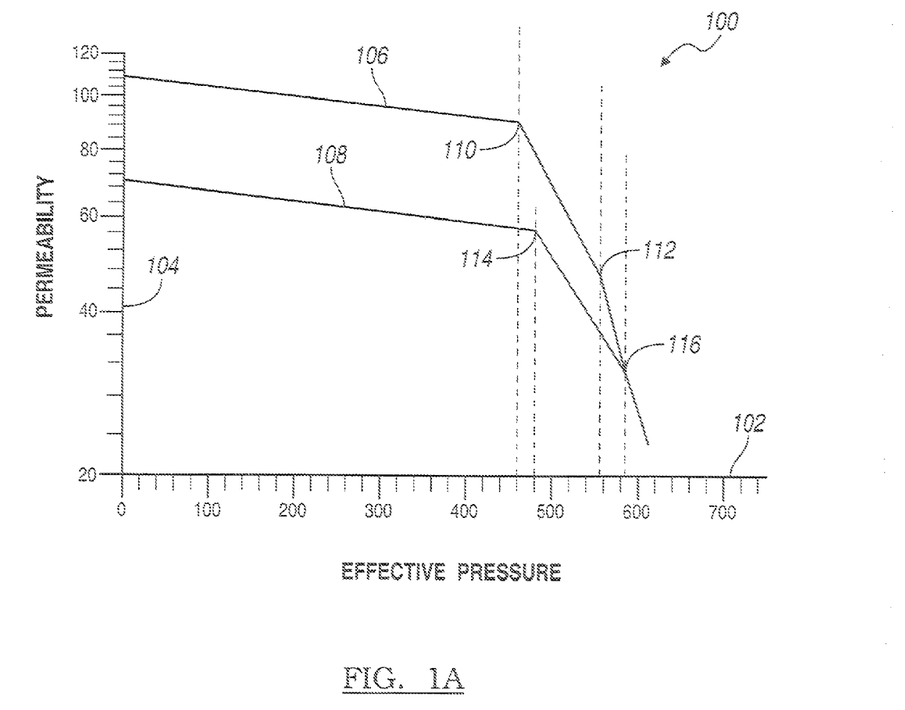
FIGS. 1A and 1B depict permeability and sonic velocity as a function of effective pressure in a geologic sample.
Figure 1B:
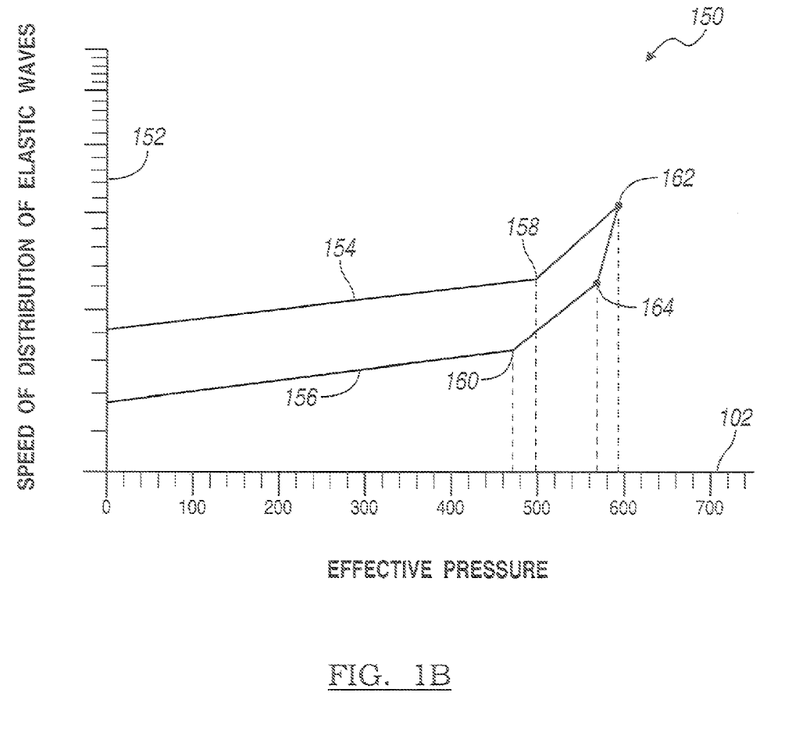

Predictive interrelationships between permeability and sonic velocity (elastic wave distribution speed) are further appreciated from consideration of FIGS. 1A and 1B. Axis of abscissas 102 is identical for both FIGS. 1A and 1B to show the effective pressure (under compression) of a geologic sample. FIG. 1A shows graph 100 of permeability (axis of ordinates 104) as a function of effective pressure (axis of abscissas 102). FIG. 1B shows graph 150 of sonic velocity (or speed of distribution of elastic waves) in axis of ordinates 152 as a function of effective pressure (axis of abscissas 102). Graph 100 shows direct course (increasing pressure for elastic status rock) readings in locus 106, with inflection point 110 showing a clear shift in the structural character of the rock where the micropores and microcracks of the rock begin to clearly collapse, an effect which intensifies from inflection point 110 to inflection point 112 where a further collapse is apparent. Inflection point 112 also provides the maximum effective pressure for augmenting petroleum removal from the bottom hole of a respective oil well for elastic rock respective to the sample used for generating data for FIGS. 1A and 1B. Locus 108 shows reverse motion (decreasing pressure for non-elastic status rock) readings, with inflection point 114 showing a clear shift in the structural character of the rock where the micropores and microcracks of the rock collapse, an effect which intensifies from inflection point 114 to inflection point 116 where increases in pressure become counterproductive. The locus between points 112 and 116 show transition from elastic to non-elastic rock.

FIG. 1B shows graph 150 of speed of distribution of elastic waves (or sonic velocity per axis of ordinates 152) as a function of effective pressure (axis of abscissas 102). Graph 150 shows direct course (increasing pressure for elastic status rock) readings in locus 156, with inflection point 160 showing a clear shift in the structural character of the rock where the micropores and microcracks of the rock begin to clearly collapse, an effect which intensifies from inflection point 160 to inflection point 164 where a further collapse is apparent. Inflection point 164 also provides the maximum effective pressure for augmenting petroleum removal from the bottom hole of a respective oil well for elastic rock respective to the sample used for generating data for FIGS. 1A and 1B. Locus 154 shows reverse motion (decreasing pressure for non-elastic status rock) readings, with inflection point 158 showing a clear shift in the structural character of the rock where the micropores and microcracks of the rock collapse, an effect which intensifies from inflection point 158 to inflection point 162 where increases in pressure become counterproductive. The locus between points 164 and 162 show transition from elastic to non-elastic rock.

FIGS. 1A and 1B have a patterned comparability with respect to linear behavior (on a semi-logarithmic scale) and inflection point location in the (semi-log) linear functions of their loci (106, 108, 154, 156). Note that the more compressed rock of lower locus 108 in view 100 of FIG. 1A is comparable to the upper locus 154 of view 150 in FIG. 1B; this is because the higher density rock (having lower permeability) transmits sound waves more readily and therefore provides a higher sonic velocity. Note also that as rock is further compressed within one of the loci, the permeability declines as the sonic velocity increases.

A comparison of FIG. 1A with FIG. 1B therefore demonstrates that, in one application, sonic behavior can be used to determine permeability once a holistic relationship for these petrophysical parameters has been established from tests where all data is taken essentially simultaneously at each particular predetermined effective pressure for a geologic sample from a particular geologic formation. In this first application, the measurement of quantitative characteristics of the rock sample occur while the load is artificially applied on the sample surface (i.e. the sample is compressed). The characteristics (geological properties) of the inner porous space (or deformability) are evaluated based on the measurement of permeability (and porosity, with permeability and porosity being measured through established and traditional methods) and speed of distribution of elastic waves of either the ultrasonic and/or aural sound range, which pass through the rock sample and thereby are in functional dependence on the effective pressure established by compression of the geologic sample. A second (in-situ) application is to measure the quantitative characteristics of the rock by means of the evaluation of the speed of distribution of elastic waves (ultrasonic and/or aural sound range) which pass through the rock at the bottom hole of a well at the creation of different layer depressions during the wellbore test. In the second application, a geologic sample does not need to be first extracted, although the probes need to be positioned in the bottom hole of the well and against the geologic formation. The permeability should be representative of the permeability in the region of the bottom hole and therefore enables a proper understanding of the optimal effective bottom hole pressure for pumping. In this regard, if the depth of the reading or sample is effectively higher than the zone of elastic deformation, the direct course dependence is used (loci 106 and 156); if the depth of the reading or sample is effectively lower than the zone of elastic deformation, the reverse course dependence is used (loci 108 and 154).

While FIGS. 1A and 1B are directed to sonic velocity measurements, electrical conductivity measurements are also believed to provide a similar predictive relationship utility in characterizing petrophysical parameters of a geologic sample from a particular geologic formation over a series of predetermined pressures.

Figure 2:
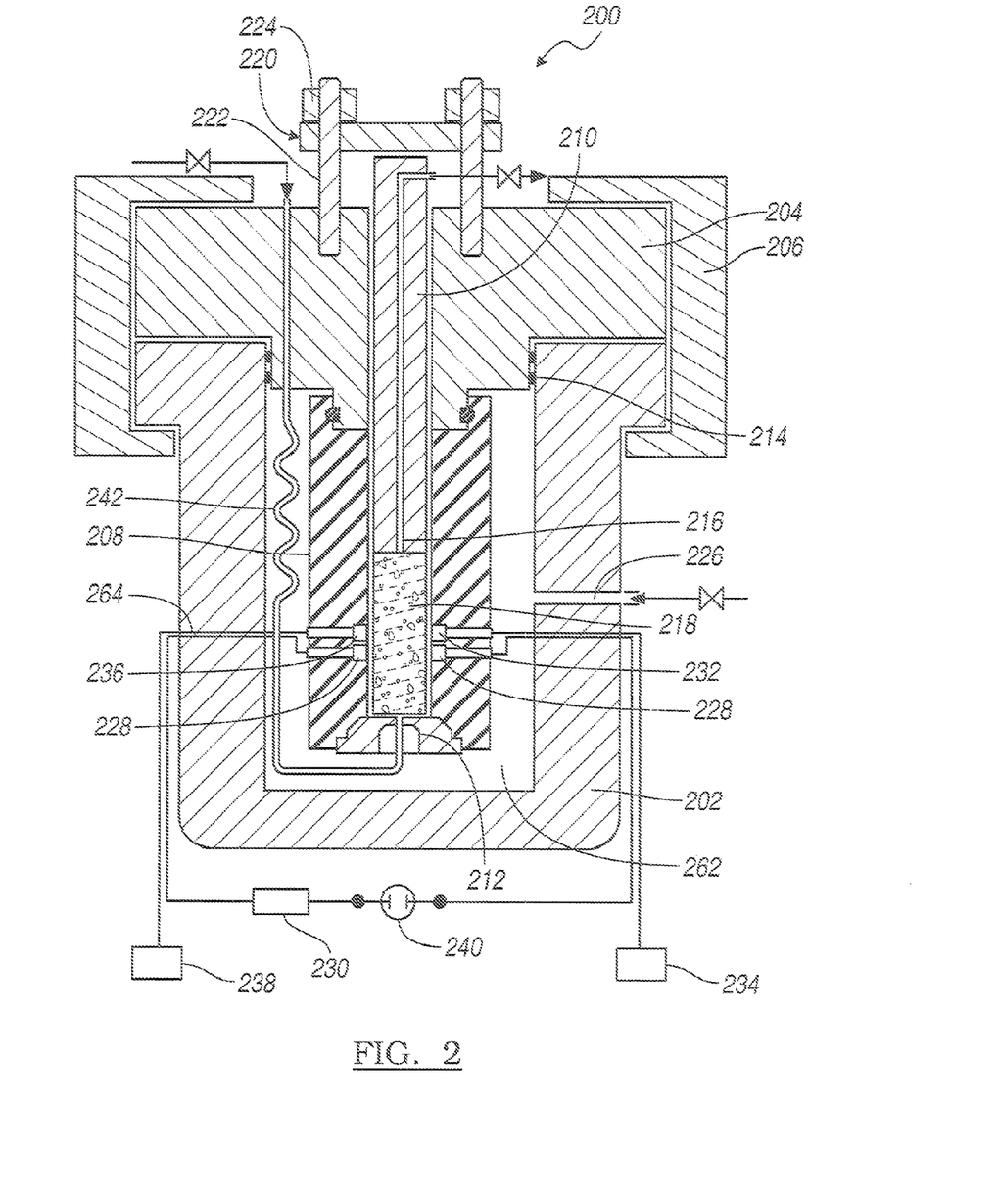
FIG. 2 shows a cross sectional view of one embodiment apparatus for measuring of petrophysical parameters of geologic samples at various pressures.

Turning now to FIG. 2, one embodiment for a testing apparatus for generating the loci (106, 108, 154, 156) of FIGS. 1A and 1B is presented in cross-sectional view 200. Positioning piston 204 is fitted to seat in casing 202 (housing 202) and is confined against casing 202 by flange 206. Rubber cuff 208 (an elastic sample container within cavity 262) is attached to an interior surface (within cavity 262 as defined by the inner surface of housing/casing 202) of positioning piston 204. Compression piston 210 fits within a channel in positioning piston 204, and the compression surface of compression piston 210 fits against one surface portion (the upper surface) of geologic sample 218. Bracket 220, stud 222, and sleeve nut 224 facilitate passive compression of compression piston 210 against the (upper) surface portion of geologic sample 218. At the base of sample 218, mobile piston 212 (preferably a conical general shape with a flattened apexial end forming a sample contact surface respective to an axis of the cone) effects active compression against the (lower) surface portion of geologic sample 218 at a sample contact surface on the end of piston 212 so that a movable piston in sealingly slideable interface to the internal surface of elastic sample container (rubber cuff) 208 is provided. Hydraulic fluid 226 fills cavity 262 between the inner surface of casing 202 and the outer surface of rubber cuff 208 and pressurizes rubber cuff 208 to pressurize sample 218 up to about 60 Pa. Expelled petroleum is removed via upper filtration channel 216 after being input via channel 242 as these channels provide a fluid conduit in fluid communication with the sample cavity of cuff 208 for conveying fluid through sample 218 as sample 218 is pressurized and permeability/porosity is thereby determined according to traditional techniques (see Background references) and correlated to sonic conductivity and/or electrical conductivity taken from transducer/sensors 228, 232, and 236. Sealing ring 214 helps to contain hydraulic fluid within casing 202. Electric contacts 228 are disposed on the inner surface of rubber cuff 208 to provide an interface for a current (AC or DC) to flow through sample 218 in a circuit powered by electrical source 240 and including resistant measuring sensor 230 for measurement of electrical characteristics of sample 218 at various pressures generated from hydraulic fluid 226. Sonic transmitter 232 and sonic receiver 236 are respectively electrically interfaced to sonic generator 234 and sonic velocity measurement instrument 238 for effecting measurement of (ultra and/or aural) sonic characteristics of sample 218 at various effective pressures generated from hydraulic fluid 226.

Energy transmitter and energy receivers (electric contacts 228, sonic transmitter 232 and sonic receiver 236, and associated wiring) are preferably installed in rubber cuff 208 at the time of manufacture of the rubber cuff. Wiring leads transit through casing 202 at sealed locations such as location 264 and are preferably isolated and insulated from hydraulic fluid contact where they transit through hydraulic fluid in pressurized regions of cavity 262. The wiring inside of cavity 262 is shown in FIG. 2 in abbreviated length; the actual wire (and its protective insulation) are preferably of sufficient length such that cuff 208 can be removed from inside casing 202 without disconnection of the wiring. Rubber cuff 208 should be sufficiently thick so that the measuring devices and the gauges (for example, without limitation, electric contacts 228, sonic transmitter 232, sonic receiver 236, and associated wiring) are sunken to be flush with the inner surface of cuff 208 and thereby provide a effectively continuous internal surface within cuff 208 for surface contact against sample 218. As should be appreciated, sample 218 is configured to snuggly fit within the sample cavity of rubber cuff 208 after piston 212 has been pressurized so that essentially all external surface portions of sample 218 are independently in contact with either the internal surface of cuff 208, the sample contact surfaces of either piston 212 or position 210, or an energy transmitter (such as one of electric contacts 228, sonic transmitter 232, or sonic receiver 236). The devices and the gauges and sample are therefore formed to mutually fit so that the sample is immediately compressed from all directions when hydraulic fluid 226 is pressurized.

In one embodiment (not shown), rubber cuff 208 is made of two parts for easier insertion of sample 218. However, this embodiment has the negative aspect of providing a possible alternate passage for the inflow of liquid to the sample in addition to that provided via channel 242 and removed through channel 216.

The apparatus of view 200 achieves triaxial compression for rock sample 218. Pressure is hydro-transmitted using the oil channel 226, cavity 262, and rubber elastic cuff 208 in the radial direction with mechanical compression (z) being imposed on sample 218 from pistons 212 and 204. Sample 218 is preferably cylindrical in form, with a diameter of from about 25 to about 30 mm and a length of from about 25 to about 40 mm.

In operation, the experimental scheme exposes geologic sample 218 to discrete (step change) pressures, with each step occurring in a time period of from about 1 hour to about 3 hours from one predetermined effective pressure to a next predetermined effective pressure (more preferably from about 1 hour to about 1.5 hours). Test oil and/or gas or a blend thereof is conveyed through sample 218 (via channels 242 and 216) so that permeability can be determined by measuring the rate of flow through sample 218 at a given effective pressure. Parameters reflecting the sample deformation are systematically measured each 15 minutes during the test run. Preferably, twenty such steps are used to characterize sample 218 over the entire range of potential effective pressures. The absolute value of the pressure is preferably maintained to be constant within a deviation of +/−2 kg/m² (atm) during the whole period of a particular stage of pressurization. The length of the sample is preferably measured with an accuracy of within 0.1 mm.; electrical conductivity is preferably measured with an accuracy of within 0.1 ohm; and the time of distribution of the sound wave (the speed of distribution of the sound wave) is preferably measured with an accuracy of within 10 microseconds.

One useful associated calculation is that the length of sample 218, the diameter of sample 218, pressure between fluid 226 and fluid expelled from channel 216, the volume of fluid expelled from channel 216, the elapsed time for passing of that fluid volume, the pressure of hydraulic compression 226, and the time of measurement are related by $$K_{np} = \frac{Q\mu L}{S\Delta P}$$

where Q is the charge of the single-phase fluid with the dynamic viscosity yμ, proceeding through the volume of rock of S section exposed to the gradient pressure ΔP/L.

Thus, the obtained data can be interpreted and be transformed into a classical rheology curve where speed of deformation is dependent on the time period at constant values of pressure and temperature, or the deformation is dependent on pressure at constant values of time and temperature.

Figure 3:
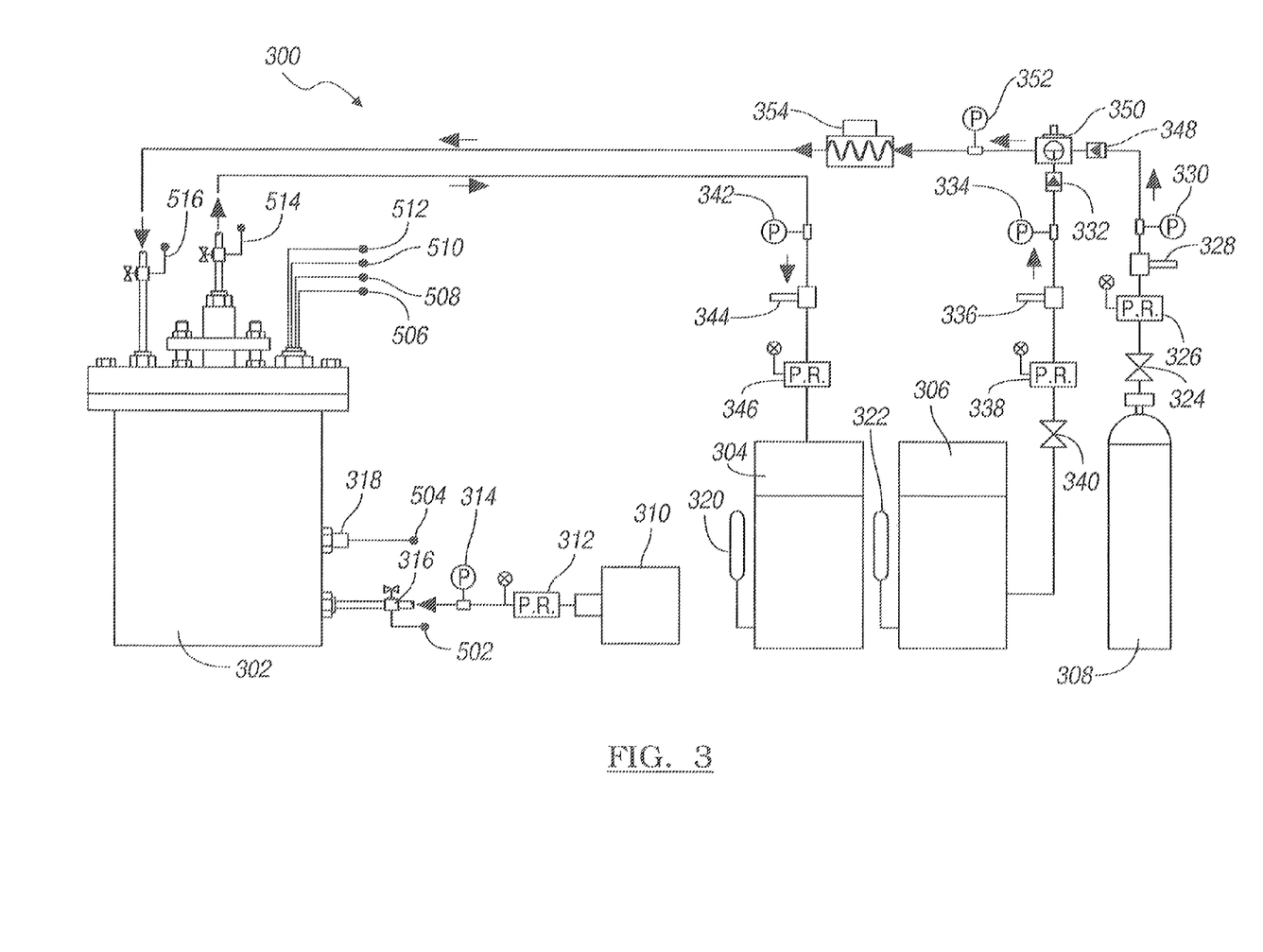
FIG. 3 shows a second embodiment of a test apparatus system for measuring of petrophysical parameters of geologic samples at various pressures.
Figure 4:
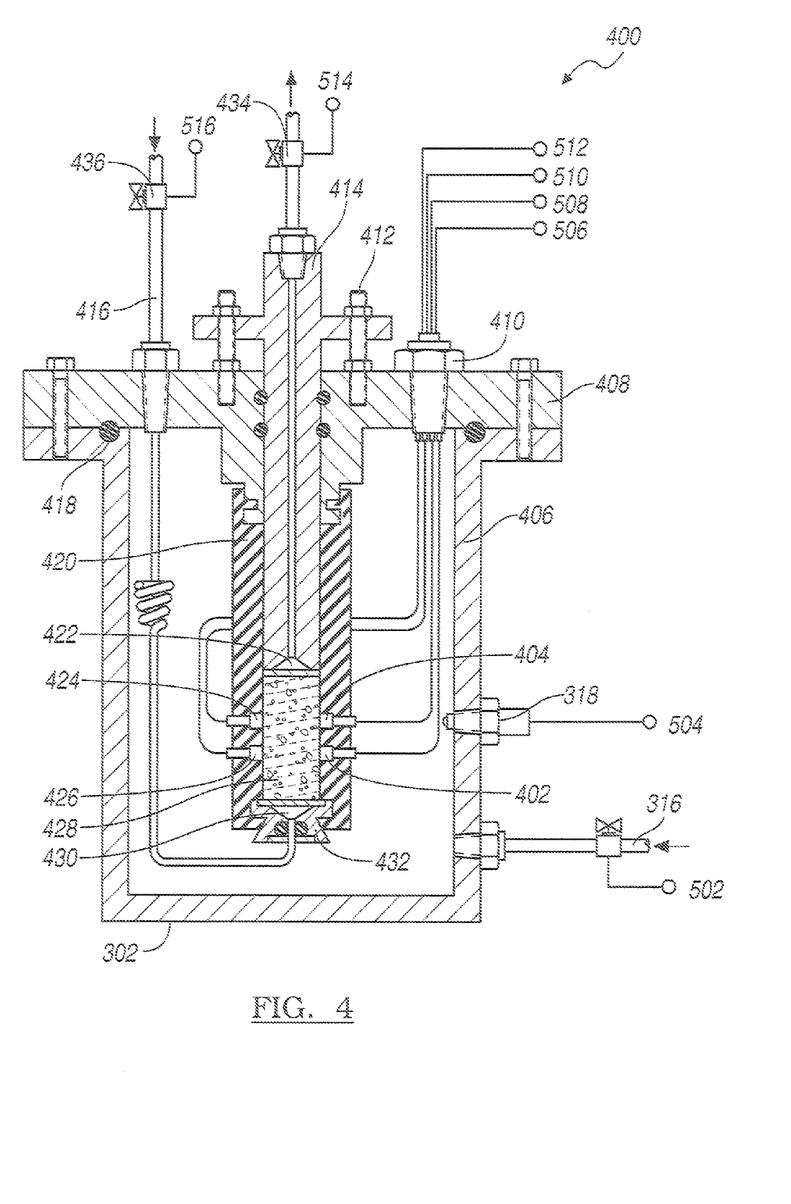
FIG. 4 shows cross-section detail in a high-pressure testing chamber used in the apparatus of FIG. 3.
Figure 5:
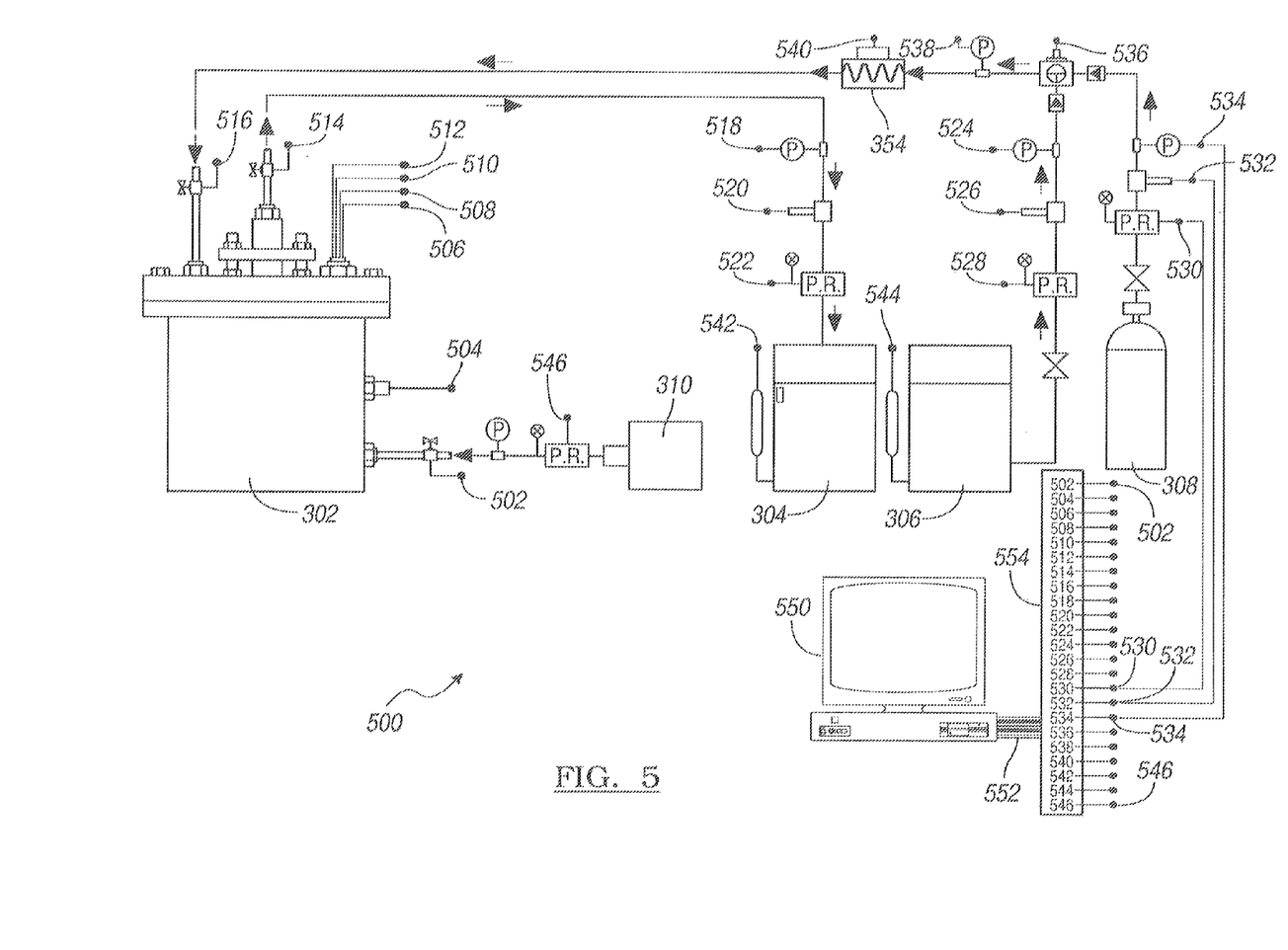
FIG. 5 shows signal linkages and a control computer for monitoring and optionally controlling the apparatus of FIGS. 3 and 4.

FIGS. 3, 4, and 5 present an alternative embodiment for a computer-facilitated testing apparatus for generating the loci (106, 108, 154, 156) of FIGS. 1A and 1B. In overview of these three Figures, FIG. 3 shows an overview 300 of operational components in the overall system; FIG. 4 shows cross sectional view 400 for detail in high pressure testing chamber 302; and FIG. 5 shows signal detail 500 in interfacing the operational components to control and/or monitoring computer 550.

Turning now to FIG. 3, overview 300 shows testing chamber 302 in fluid interface with pressurization pump 310 via line pressure regulator 312, pressurization pump line pressure sensor 314, and chamber pressure control valve 316. Hydraulic fluid pressure is monitored via test chamber pressure sensor 318. Testing chamber 302 is in receiving fluid interface with petroleum oil (or other test oil) from test oil supply tank 306 and/or gas from gas supply cylinder 308. Test oil supply tank 306 fluidly interfaces to testing chamber 302 via oil supply flow regulator 340, oil supply flow pressure regulator 338, oil supply flow rate sensor 336, oil supply flow line pressure sensor 334, check valve 332, mixing chamber 350, feed fluid pressure sensor 352, and heat exchanger 354. Gas supply cylinder 308 fluidly interfaces to testing chamber 302 via gas cylinder regulating valve 324, gas cylinder pressure regulator 326, gas cylinder flow rate sensor 328, gas cylinder flow line pressure sensor 330, check valve 348, mixing chamber 350, feed fluid pressure sensor 352, and heat exchanger 354. Testing chamber 302 is also in discharging fluid interface with exit liquid receiving tank 304 via exit fluid flow line pressure sensor 342, exit fluid flow rate sensor 344, and exit fluid pressure regulator 346. Receiving tank level sensor 320 is a level monitoring sensor in exit liquid receiving tank 304; test oil level sensor 322 is a is a level monitoring sensor in test oil supply tank 306.

FIG. 4 shows cross sectional view 400 for detail in high-pressure test chamber 302. Sample oil from exit liquid receiving tank 304 and/or gas from gas supply cylinder 308 enter testing chamber 302 through test fluid feed channel control valve 436 and test fluid entry channel 416 to pass through geologic sample 428 via feed fluid distribution cone 430 in compression cuff sealing plug 432. Discharge from geologic sample 428 passes through exit flow collection cone 422, conveys through a channel in sample chamber upper compression piston 414, exits from testing chamber 302 via exit fluid channel control valve 434, and is fluidly conveyed to exit liquid receiving tank 304. Test chamber sealing o-ring 418 helps to contain pressurized hydraulic fluid within the internal chamber defined by the inner surfaces of chamber casing 406 and chamber top 408. Fastening compression bolts such as sample holder compression bolt 412 compress sample chamber upper compression piston 414 against geologic sample 428 and also allow for removal of geologic sample 428 from within elastic compression cuff 420. Sonic wave source transducer 404 and sonic wave receiving sensor 424 co-operate to measure sonic wave propagation data values as sample 428 is tested at various pressures; positive electrical conductivity pole 402 and negative electrical conductivity pole 426 co-operate to measure electrical conductivity data values across sample 428 as sample 428 is tested at various pressures. Signal lines from positive electrical conductivity pole 402, sonic wave source transducer 404, sonic wave receiving sensor 424, and negative electrical conductivity pole 426 pass through chamber top 408 with benefit of sealing from sensor wire sealing grommet 410 to become signal I/O to computer 550 (FIG. 5) as positive electrical voltage 506, sonic wave source signal 508, sonic wave measurement 510, and negative electrical signal 512. Test fluid inlet pressure control signal 516 is a signal output from computer 550 to control test fluid feed channel control valve 436. Chamber pressure regulation signal line 502 is a signal output from computer 550 to control pressure control valve 316. Fluid pressure exit control signal 514 is a signal output from computer 550 to control exit fluid channel control valve 434.

FIG. 5 shows signal detail 500 in interfacing the operational components to control and/or monitoring computer 550. Computer 550 includes computer executable logic (software and other application programs) for monitoring input signals from sensors measuring values, states, and characteristics of testing apparatus of overview 300. These signals pass through general interface wiring (summarily indicated as drawing element 554 and connection cable 552) to I/O cards of computer 550. Computer 550 also includes computer executable logic (software and other application programs) for controlling output signals to actuators for modifying the positional state of control elements in the testing apparatus of overview 300. Test chamber pressure regulator control signal 546 electrically interfaces line pressure regulator 312 to computer 550 to provide a control signal from computer 550 to the testing apparatus. Chamber pressure measurement signal line 504 electrically interfaces test chamber pressure sensor 318 to computer 550 to provide a measurement signal into computer 550. Exit liquid pressure measurement signal 518 electrically interfaces exit fluid flow line pressure sensor 342 to computer 550 to provide a measurement signal into computer 550. Exit liquid pressure control signal 522 electrically interfaces exit fluid pressure regulator 346 to computer 550 to provide a control signal from computer 550 to the testing apparatus. Receiving tank level measurement signal 542 electrically interfaces receiving tank level sensor 320 to computer 550 to provide a measurement signal into computer 550. Test oil tank level measurement signal 544 electrically interfaces test oil level sensor 322 to computer 550 to provide a measurement signal into computer 550. Test liquid pressure control signal 528 electrically interfaces oil supply flow pressure regulator 338 to computer 550 to provide a control signal from computer 550 to the testing apparatus. Test liquid pressure measurement signal 524 electrically interfaces oil supply flow line pressure sensor 334 to computer 550 to provide a measurement signal into computer 550. Feed fluid mixture pressure measurement signal 538 electrically interfaces feed fluid pressure sensor 352 to computer 550 to provide a measurement signal into computer 550. Test gas pressure control signal 530 electrically interfaces gas cylinder pressure regulator 326 to computer 550 to provide a control signal from computer 550 to the testing apparatus. Test gas pressure measurement signal 534 electrically interfaces gas cylinder flow line pressure sensor 330 to computer 550 to provide a measurement signal into computer 550. Test gas flow rate measurement signal 532 electrically interfaces gas supply flow rate sensor 328 to computer 550 to provide a measurement signal into computer 550. Exit liquid flow rate measurement signal 520 electrically interfaces exit fluid flow rate sensor 344 to computer 550 to provide a measurement signal into computer 550. Test liquid flow rate measurement signal 526 electrically interfaces oil supply flow rate sensor 336 to computer 550 to provide a measurement signal into computer 550. Chamber pressure regulation signal line 502 electrically interfaces pressure control valve 316 to computer 550 to provide a control signal from computer 550 to the testing apparatus. Test fluid inlet pressure control signal 516 electrically interfaces test fluid feed channel control valve 436 to computer 550 to provide a control signal from computer 550 to the testing apparatus. Fluid pressure exit control signal 514 electrically interfaces exit fluid channel control valve 434 to computer 550 to provide a control signal from computer 550 to the testing apparatus. Temperature control and measurement signals 540 electrically interface heat exchanger 354 to computer 550 to provide measurement and control signals from computer 550. Mixer control regulation signal 536 electrically interfaces mixing chamber 350 to computer 550 to provide measurement and control signals from computer 550.

As will be appreciated from a study of FIGS. 3-5, both gas and test oil permeability, sonic, and electrical conductivity data can be acquired from sample 428 through use of the test apparatus according to the general procedures described with respect to operation of the apparatus of FIG. 2. Through use of mixer 536, various blends of gas and test oil can also be evaluated. In this regard, the petroleum deposits of interest frequently provide both gas and oil minerals for harvesting. Commercially available monitoring and control software such as, for example, LabView™ software, is used in one embodiment to monitor and control pressure, temperature, and flows in the test system including the sample chamber in the experimental set-up.

It will be understood that each of the elements described above, or two or more together, may also find a useful application in other types of methods and constructions differing from the types described above. While the invention has been illustrated and described as embodied in the method of and apparatus for producing methanol, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention. What is claimed as new and desired to be protected by Letters Patent is set forth in the appended claims.

What is claimed is:

1. A method for determining petrophysical parameters within a geologic formation, comprising:
   obtaining a geologic sample from said geologic formation;
   pressurizing said geologic sample to a predetermined effective pressure;
   energizing said geologic sample at said predetermined effective pressure with an energy wave;
   measuring a conductivity value in said geologic sample respective to said energizing at said predetermined effective pressure; and
   repeating said pressurizing, energizing, and measuring steps over a number of predetermined effective pressures to provide a set of conductivity measurements as a function of said predetermined effective pressures for said geologic sample.

2. The method of claim 1 wherein said geologic formation has an elastic deformation depth value, said obtaining further measures the depth of said geologic sample in said geologic formation, and, in said repeating, the predetermined effective pressures incrementally increase when said geologic sample depth is less than said elastic deformation depth value.

3. The method of claim 1 wherein said geologic formation has an elastic deformation depth value, said obtaining further measures the depth of said geologic sample in said geologic formation, and, in said repeating, the predetermined effective pressures incrementally decrease when said geologic sample depth is greater than said elastic deformation depth value.

4. The method of claim 1 wherein said energy wave comprises an electric current and said conductivity value comprises electrical conductivity.

5. The method of claim 1 wherein said energy wave is a sonic wave and said conductivity value comprises sonic velocity.

6. The method of claim 1 wherein said set of conductivity measurements as a function of predetermined effective pressures has an affiliated inflection point defining a maximum effective pressure for said geologic formation.

7. The method of claim 1 wherein a porosity measurement of said geologic formation is measured at each said predetermined effective pressure to provide a set of porosity measurements as a function of predetermined effective pressures for said geologic sample.

8. The method of claim 1 wherein said pressurizing comprises uniaxial compression.

9. The method of claim 1 wherein said pressurizing comprises triaxial compression.

10. The method of claim 1 wherein both an electric current energy wave and a sonic wave energy wave are used in said energizing.

11. The method of claim 10 wherein said measuring further comprises measuring electrical conductivity of said sample respective to said electric current energy wave, and measuring sonic velocity of said sample respective to said sonic wave energy wave.

12. The method of claim 1 wherein a permeability measurement of said geologic formation is determined at each said predetermined effective pressure to provide a set of permeability measurements as a function of predetermined effective pressures for said geologic sample.

13. The method of claim 12 wherein said geologic sample is a first geologic sample, said method further comprising positioning a sonic transmitter and sonic receiver at a depth in said geologic formation; measuring a test conductivity value at said evaluating effective pressure; and defining a permeability value for said geologic formation using said test conductivity value, said set of permeability measurements, and said set of conductivity measurements.

14. The method of claim 12 wherein said geologic sample is a first geologic sample, said method further comprising obtaining a second geologic sample from a depth in said geologic formation; pressurizing said second sample to an evaluating effective pressure representative of pressure at said depth; measuring a test conductivity value at said evaluating effective pressure; and defining a permeability value for said second geologic sample using said test conductivity value, said set of permeability measurements, and said set of conductivity measurements.

15. An apparatus for measuring fluid flow capability within a geologic sample, comprising:
a housing having a housing inner surface defining a housing cavity;
an elastic sample container within said cavity, said elastic sample container having an sample container internal surface and a movable piston in sealingly slideable interface to said internal surface, said piston having a sample contact surface, and said sample container providing a sample cavity thereby with said sample container internal surface and said sample contact surface;
a hydraulic fluid in hydraulic linkage to said piston and disposed within said housing cavity to encapsulate said elastic sample container;
at least one energy transmitter disposed on a first portion of said sample container internal surface;
at least one energy receiver disposed on a second portion of said sample container internal surface;
a fluid conduit in fluid communication with said sample cavity for expelling fluid from said sample cavity;
means for energizing said at least one transmitter;
means for measuring an energy signal from said at least one energy receiver; and
means for pressurizing said hydraulic fluid;
wherein said sample is configured to snuggly fit within said sample cavity after said piston has been pressurized so that essentially all external surface portions of said sample are independently in contact with one of said internal surface, said sample contact surface, a said energy transmitter, and a said energy receiver.

16. The apparatus of claim 15 wherein said energy transmitter comprises an electrical contact, said energy receiver comprises an electrical contact, and said means for measuring an energy signal determines electrical conductivity across said sample.

17. The apparatus of claim 15 wherein said energy transmitter comprises a sonic transmitter, said energy receiver comprises a sonic receiver, and said means for measuring an energy signal determines sonic velocity through said sample.

18. The apparatus of claim 15 wherein a first said energy transmitter comprises an electrical contact, a first said energy receiver comprises an electrical contact, a first said means for measuring an energy signal determines electrical conductivity across said sample, a second said energy transmitter comprises a sonic transmitter, a second said energy receiver comprises a sonic receiver, and a second said means for measuring an energy signal determines sonic velocity through said sample.

19. The apparatus of claim 15 further comprising means for determining a porosity measurement of said geologic sample.

20. The apparatus of claim 15 further comprising means for determining a permeability measurement of said geologic sample.

* * * * *